United States Patent [19]
Candau

[11] Patent Number: 6,033,648
[45] Date of Patent: Mar. 7, 2000

[54] ARTIFICIAL TANNING COMPOSITIONS COMPRISING IRON OXIDE NANOPIGMENTS

[75] Inventor: Didier Candau, Bievres, France

[73] Assignee: Societe L'OREAL S.A., Paris, France

[21] Appl. No.: 09/344,354

[22] Filed: Jun. 25, 1999

[30] Foreign Application Priority Data

Jun. 26, 1998 [FR] France .................................. 98 08164

[51] Int. Cl.⁷ ............................. A61K 7/42; A61K 7/44; A61K 7/00
[52] U.S. Cl. ................................. 424/59; 60/400; 60/401
[58] Field of Search .......................... 424/59, 60, 400, 424/401

[56] References Cited

U.S. PATENT DOCUMENTS

| 5,547,658 | 8/1996 | Hansenne et al. |
| 5,741,480 | 4/1998 | Ascione . |

FOREIGN PATENT DOCUMENTS

| 0669125 | 8/1995 | European Pat. Off. . |
| 2703247 | 10/1994 | France . |
| 93/11742 | 6/1993 | WIPO . |
| 94/21221 | 9/1994 | WIPO . |

OTHER PUBLICATIONS

Seifen, Ole, Fette, Wachse, vol. 98, No. 16, 1972, p. 512, lines 29–44.

*Primary Examiner*—Shelley A. Dodson
*Attorney, Agent, or Firm*—Burns, Doane, Swecker & Mathis, L.L.P.

[57] ABSTRACT

Topically applicable cosmetic/dermatological compositions well suited for the persistent and water-resistant artificial tanning and/or darkening of human skin, comprise an effective artificial tanning/darkening amount of particulates of at least one iron oxide nanopigment, the mean size of the primary particles of which nanopigment particulates being less than 100 nm, the particulates of the at least one iron oxide nanopigment being formulated into a vehicle, diluent or carrier therefor which comprises a water-in-oil emulsion, advantageously a water-in-silicone emulsion, and the particulates comprising greater than 2% by weight of the total weight of such cosmetic/dermatological compositions.

23 Claims, No Drawings

ARTIFICIAL TANNING COMPOSITIONS COMPRISING IRON OXIDE NANOPIGMENTS

CROSS-REFERENCE TO PRIORITY APPLICATION

This application claims priority under 35 U.S.C. § 119 of FR-98/08164, filed Jun. 26, 1998, hereby expressly incorporated by reference.

BACKGROUND OF THE INVENTION

1. Technical Field of the Invention

The present invention relates to novel cosmetic and/or dermatological compositions comprising at least one iron oxide nanopigment, well suited for artificially tanning and/or darkening human skin to such extent as to resemble a natural tan.

2. Description of the Prior Art

Today, many consumers seek to retain a healthy appearance and desire a tanned skin. However, natural tanning is not always desirable insofar as it requires prolonged exposure to UV radiation, in particular to UV-A radiation, which promotes browning of the skin but, on the other hand, can induce a detrimental change in the latter, in particular in the case of sensitive skin or of skin continually exposed to solar radiation. It is therefore desirable to provide an alternative to natural tanning which is compatible with the requirements of such skin.

The majority of cosmetic products suited for the artificial tanning of the skin are based on carbonyl compounds which enable the formation of colored species by interaction with the amino acids of the skin.

To this end, it is known to this art that dihydroxyacetone, or DHA, is a particularly advantageous active species which is commonly used in cosmetics as an agent for the artificial tanning of the skin; applied to the skin, in particular to the face, it makes it possible to obtain a tanning or browning effect with an appearance similar to that which can result from prolonged exposure to the sun (natural tanning) or under a UV lamp.

However, the use of DHA can present certain disadvantages. Thus, DHA has an unfortunate tendency, more or less pronounced depending on the nature of the medium in which it is formulated, to decompose over time, this decomposition generally being reflected in the long run by an undesirable yellowing of the compositions in which it is present. Such a phenomenon indicates that the activity of the DHA, in particular its ability to color the skin, may be decreased at the time of the application of these compositions onto the skin. Thus, the intensity of the coloration imparted to the skin may appear to remain insufficient.

Another disadvantage of DHA is the slowness with which the coloration develops: this is because several hours (3 to 5 hours in general) are required for the coloring to develop. Furthermore, the coloring produced on the skin with DHA is often regarded as too yellow by users.

Responding to this need, it has been suggested to combine DHA with various compounds: thus, WO-95/15742 describes the combination of DHA with amino acids. However, such combinations are very little used in practice insofar as such use requires either a two-step application or complex separate packagings. FR-2,726,761 describes, for its part, the combination of DHA with lawsone and/or juglone; here again, this combination is not very satisfactory, due this time to the risks of sensitization which it exhibits.

Thus, serious need continues to exist for novel compounds and novel compositions which make it possible to artificially confer on the skin a coloration similar to natural tanning in a simple, efficient, rapid and risk-free manner.

Iron oxide pigments have long been known for their superficial and short-lived covering and coloring properties on human skin. They are generally formulated into makeup products, such as foundations, mascaras, eyeliners and lipsticks. Their mean size generally ranges from 0.2 to 50 $\mu$m depending on the desired coloring effects and the application envisaged. Exemplary of the makeup compositions comprising same are described in WO-94/15580, WO-96/36309, WO-96/33690, WO-96/36323 and FR-A-2,754,708.

Iron oxide nanoparticles (hereinafter referred to as iron oxide nanopigments) having a mean size of less than 200 nm are generally used for their good properties of screening UV radiation over a large spectrum in the formulation of cosmetic compositions, such as those described in FR-A-2,746,301 and FR-A-2,746,301. They are also present in sun protection products based on titanium or zinc oxide nanopigments, in order to lighten or mask the blue color resulting from photobluing under the influence of UV radiation, as described in WO-93/11742.

SUMMARY OF THE INVENTION

It has now unexpectedly been determined that iron oxide nanopigments, formulated into a water-in-oil emulsion vehicle, diluent or carrier, imparted to the skin, a few minutes after application thereto, an artificial coloring similar to natural tanning which is simultaneously intense, non-covering (namely, not having a tendency to opacify the skin) and transparent. The colorations provided by these specific emulsions are furthermore persistent over time and particularly resistant to water.

The present invention thus features novel cosmetic and/or dermatogical compositions well suited for imparting to human skin an artificial coloration similar to natural tanning, comprising in a vehicle, diluent or carrier in the form of a water-in-oil emulsion, greater than 2% by weight with respect to the weight of said composition of at least one iron oxide nanopigment, the mean size of the primary particles of which being less than 100 nm.

DETAILED DESCRIPTION OF BEST MODE AND SPECIFIC/PREFERRED EMBODIMENTS OF THE INVENTION

More particularly according to the present invention, by the term "composition suited for the artificial coloring of the skin" is intended a formulation having a specific affinity for the skin which allows it to impart thereto a durable coloration which is removed neither with water nor with a solvent and which withstands both rubbing and washing with a solution containing surfactants. Such a durable coloration is therefore distinguished from the superficial and short-lived coloration contributed, for example, by a makeup product.

The iron oxide nanopigments according to this invention generally have a mean primary particle size preferably ranging from 5 nm to 50 nm and more particularly from 10 to 30 nm. They are present in the compositions of the invention in proportions of greater than 2% by weight and preferably ranging up to 10% by weight and more particularly ranging from 3% to 6% by weight with respect to the total weight of the composition.

Exemplary such iron oxide nanopigments include:

(1) transparent yellow iron oxide (needles of 10 nm×100 nm), marketed under the trademark "Cappoxyt jaune 4214 X" [Cappoxyt yellow 4214 X] by Capelle;

(2) transparent red iron oxide (needles of 10 nm×100 nm), marketed under the trademark "Cappoxyt jaune 4435 B" [Cappoxyt yellow 4435 B] by Capelle;

(3) sstearin-coated yellow iron oxide (10 nm), marketed as "oxyde de fer transparent" [transparent iron oxide] by BASF;

(4) micronized yellow iron oxide marketed under the trademark "TY-220" by Mitsubishi;

(5) red iron oxides of the a type (3 nm), marketed under the references "Nanocat superfine iron oxide" and "Nanocat SFIO rouge dispersion in mineral oil" by Mach 1;

(6) uncoated brown iron oxide (26 nm), marketed under the trademark "Nanoguard WCD 2002" by Nanophase Technologies;

(7) uncoated red iron oxide (26 nm), marketed under the trademark "Nanoguard WCD 2006" by Nanophase Technologies;

(8) black iron oxide as a 50% aqueous dispersion (23 nm), marketed under the trademark "Nanoguard Iron FE45BL AQ" by Nanophase Technologies;

(9) coated red iron oxide as a 40% dispersion in the silicone material DC345 (31 nm), marketed under the trademark "Nanoguard WCD 2015" by Nanophase Technologies;

(10) black iron oxide (23 nm), marketed under the trademark "Nanoguard FE45BL" by Nanophase Technologies;

(11) brown iron oxide as a 40% dispersion in the silicone material DC556 (26 nm), marketed under the trademark "Nanoguard WCD 2008" by Nanophase Technologies;

(12) brown iron oxide as a 40% dispersion in Finsolv TN (26 nm), marketed under the trademark "Nanoguard WCD 2009" by Nanophase Technologies;

(13) red iron oxide as a 50% aqueous dispersion (23 nm), marketed under the trademark "Nanoguard Iron FE45R AQ" by Nanophase Technologies.

The compositions according to the invention are formulated as water-in-oil emulsions and generally contain a continuous oily phase which can comprise one or more fatty substances, it being possible for these fatty substances to be an oil, or a wax, or mixture thereof.

By the term "oil" is intended an oily compound which is liquid at ambient temperature. By the term "wax" is intended a waxy compound which is solid or substantially solid at ambient temperature and for which the melting point is generally greater than 35° C.

Exemplary oils according to the invention include oils of vegetable or animal, mineral or synthetic origin; fluorinated oils; $C_{12}$–$C_{18}$ fatty acid triglycerides; volatile or non-volatile silicone oils and mixtures thereof.

Exemplary oils of animal or vegetable origin include, modified or otherwise, sweet almond oil, avocado oil, castor oil, olive oil, jojoba oil, sunflower oil, wheat germ oil, sesame oil, groundnut oil, grape seed oil, soybean oil, rapeseed oil, safflower oil, coconut oil, maize oil, hazelnut oil, karite butter, palm oil, (apricot) kernel oil or calophyllum oil.

Representative oils of mineral origin, include the liquid paraffins.

And exemplary synthetic oils include, in particular, volatile or non-volatile isoparaffins and polyisobutenes.

Exemplary waxes according to this invention include waxes of animal origin, such as lanolin, beeswax, spermaceti or lanolin derivatives, such as lanolin alcohols, hydrogenated, hydroxylated or acetylated lanolin, lanolin fatty acids and acetylated lanolin alcohols; waxes of vegetable origin, such as carnauba, candelilla, kapok, ouricury, rice, hydrogenated jojoba, esparto or japan wax or cork fiber or sugar cane waxes or cocoa butter; mineral waxes, for example paraffin, montan, lignite or petrolatum wax, petroleum jelly or microcrystalline waxes, ceresin or ozokerite; or synthetic waxes, such as polyethylene waxes, waxes obtained by the Fischer-Tropsch synthesis and linear esters resulting from the reaction of a saturated $C_{10}$ to $C_{40}$ carboxylic acid with a saturated $C_{10}$ to $C_{40}$ alcohol, such as myristyl myristate. Cetyl alcohol, stearyl alcohol, calcium lanolates or stearates, castor oil, palm oil, coconut oil, sunflower oil and hydrogenated coconut oil are also suitable.

And exemplary silicone oils according to the invention include optionally functionalized linear polydiorganosiloxanes, or cyclic polydiorganosiloxanes, or optionally crosslinked organopolysiloxanes, or mixtures thereof.

By the term "silicone" is intended, in conformity with generally accepted definitions, any organosilicon polymer or oligomer having a linear or cyclic, branched or crosslinked structure, of variable molecular weight, obtained by polymerization and/or polycondensation of suitably functionalized silanes and essentially composed of recurring structural units in which the silicon atoms are bonded to one another via oxygen atoms (siloxane bond ≡Si—O—Si≡), optionally substituted hydrocarbon-comprising radicals being directly bonded via a carbon atom to said silicon atoms. The most common hydrocarbon-comprising radicals are alkyl radicals,. in particular $C_1$–$C_{10}$ alkyl radicals and especially the methyl radical, fluoroalkyl radicals or aryl radicals and in particular the phenyl radical. These can be substituted, for example, by $C_1$–$C_{40}$ ester or ether groups or $C_7$–$C_{60}$ aralkyl groups.

Representative silicone oils comprising optionally functionalized linear polydiorganosiloxanes according to the invention have the following structural formula:

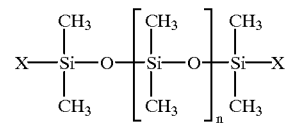

in which X is —$CH_3$ or OH, and n is an integer ranging from 0 to 2,000.

Exemplary of such silicones are the products marketed under the trademarks "AK" by Wacker, "SF" by General Electric and "Abil" by Goldschmidt, such as the product "Abil 10".

Representative cyclic polydiorganosiloxanes according to the invention, whether alone or in admixture, comprise the cyclomethicones having the formula:

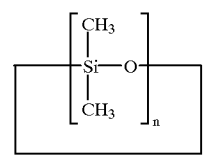

in which n is an integer ranging from 3 to 8.

Particularly preferred such cyclomethicones include cyclotetradimethylsiloxane (n=4), cyclopentadimethylsiloxane (n=5) and cyclohexadimethylsiloxane (n=6).

Also preferred are the silicones marketed under the trademarks "DC Fluid 244", "DC Fluid 245", "DC Fluid 344 and "DC Fluid 345" by Dow Corning.

Other cyclomethicones which are suitable according to the invention are those marketed under the trademark "Abil K4" by Goldschmidt; under the trademarks "Silbione 70045 V2" and "Silbione Huile 70045 V5" [Silbione Oil 70045 V5] by Rhône-Poulenc; and under the trademarks "Volatil Silicone 7158" and "Volatil Silicone 7207" by Union Carbide.

The compositions of the invention can also comprise other silicone compounds such as poly($C_1$–$C_{20}$) alkylsiloxanes, including phenylated silicone oils, as well as silicone gums and silicone waxes.

The silicone gums which can be formulated into the compositions of the invention can be polysiloxanes of high molecular weight, on the order of 200,000 to 1,000,000, and having a viscosity of greater than 500,000 mPa·s. They can be used alone or in admixture with a solvent, such as a polydimethylsiloxane or polyphenylsiloxane oil, or a cyclomethicone.

The silicone waxes which can be formulated into the composition according to the invention can be substituted linear polysiloxanes. Exemplary thereof are silicone polyether waxes or alkyl or alkoxy dimethicones having from 16 to 45 carbon atoms.

The compositions according to the invention can also contain silicone resins comprising a combination of the $R_3SiO_{1/2}$, $R_2SiO_{2/2}$, $RSiO_{3/2}$, and $SiO_{4/2}$ structural units.

In a particularly preferred embodiment of the invention, the subject compositions are formulated as water-in-silicone emulsions in which the continuous oily phase comprises at least one silicone oil as described above. Particularly representative of such oils are volatile silicone oils, such as cyclomethicones, in order to impart greater fastness towards water of the coloration on the skin, easier and more homogeneous spreading of the composition and shorter drying times.

When the compositions of the invention are formulated as water-in-silicone emulsions, the silicone oils are preferably present in a proportion of at least 5% and preferably ranging from 10% to 45% by weight with respect to the total weight of the emulsion. The fatty phase of the water-in-oil emulsions according to the invention can additionally comprise one or more hydrocarbon-comprising oil(s) in a proportion preferably ranging up to 40% by weight with respect to the total weight of the fatty phase of the emulsion.

The compositions of this invention preferably comprise a silicone emulsifier that is a polyalkylpolyethersiloxane substituted by polyoxyethylene and polyoxypropylene chains grafted onto the main or backbone chain or at the ends of the main chain.

This silicone emulsifier is advantageously selected from among the compounds having the following structural formula (I):

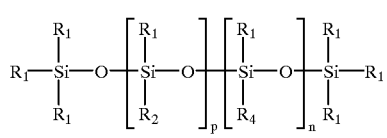

(I)

in which $R_1$ and $R_4$, which may be identical or different, are each a hydrogen atom, a linear or branched $C_1$–$C_{30}$ alkyl radical or a phenyl radical; the radicals $R_2$, which may be identical or different, are each —$(C_xH_{2x})$—$(OC_2H_4)_a$—$(OC_3H_6)_b$—$OR_3$, wherein the radicals $R_3$, which may be identical or different, are each a hydrogen atom, a linear or branched alkyl radical having from 1 to 12 carbon atoms, or a linear or branched acyl radical having from 2 to 12 carbon atoms; n ranges from 1 to 1,000; p ranges from 1 to 30; a ranges from 1 to 50; b ranges from 1 to 50; and x ranges from 1 to 5.

The number-average molecular weight of these silicone emulsifiers is generally greater than or equal to 15,000 and preferably ranges from 20,000 to 40,000.

A first category of polyalkylpolyethersiloxanes which is particularly well suited for inclusion in the compositions according to the invention is that of the compounds corresponding to the above formula (I) in which the $R_1$, and $R_4$ radicals are identical and each represents a methyl radical and the $R_3$ radical is a hydrogen atom.

Exemplary silicone emulsifiers belonging to this category are the oxyethylenated-oxypropylenated (EO/PO 18/18) polydimethyl/methylsiloxane in which n is 396 and p is 4, having a number-average molecular weight of greater than 30,000 (CTFA name: Cyclomethicone 90% Dimethicone copolyol 10%), marketed under the trademark "Silicone Q2-3225C" by Dow Corning.

In the above definition and hereinafter, EO represents one mole of ethylene oxide and PO represents one mole of propylene oxide.

A second category of polyalkylpolyether-siloxanes which is particularly well suited for inclusion in the compositions according to the invention is that of the compounds corresponding to the above formula (I) in which the $R_1$ radicals are each a methyl radical and the R4 radicals are each a lauryl radical.

A particularly preferred silicone emulsifier of this second category is the oxyethylenated-oxypropylenated (EO/PO 18/18) polymethyllauryl/methylsiloxane in which n is 35 and p is 3, having a number-average molecular weight of greater than 25,000 (CTFA name: Laurylmethicone copolyol 91%, Isostearyl alcohol 9%), marketed under the trademark "DC Q2-5200" by Dow Corning.

A silicone emulsifier which is very particularly preferred for inclusion in the compositions according to the invention is an oxyalkylene silicone substituted at the α- and ω-positions, having a linear structure, substituted at the two ends of the main chain by oxyalkylene groups bonded to the Si atoms via a hydrocarbon-comprising group. More particularly preferred are the silicones having the the following structural formula (II):

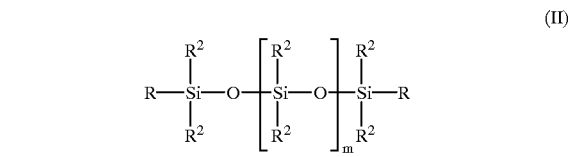

(II)

in which R is a radical —$(CH_2)_sO$—$(C_2H_4O)_t(C_3H_6O)_uR^1$ wherein $R^1$ is H, $CH_3$ or $CH_2CH_3$, s is an integer ranging from 1 to 5, t ranges from 1 to 100 and u ranges from 0 to 50, with the proviso that the ($C_2H_4O$) and ($C_3H_6O$) structural units may be distributed randomly or in blocks, the $R^2$ radicals are each a $C_1$–$C_3$ alkyl radical or a phenyl radical, and $5 \geq m \geq 300$.

The oxyalkylenated silicones substituted at the α- and ω-positions according to the present invention preferably have the formula (II) in which each of the $R^2$ radicals is a methyl radical, s ranges from 2 to 4; t ranges from 3 to 100; and m ranges from 50 to 200.

More preferably, the average molecular weight of R ranges from 800 to 2,600.

The ratio by weight of the $C_2H_4O$ units with respect to the $C_3H_6O$ units preferably ranges from 100:10 to 20:80. This ratio is advantageously approximately 42/58.

More preferably, $R^1$ is the methyl group.

Even more preferably, the emulsions according to the invention comprised the oxyalkylenated silicone at the α- and ω-positions having the following structural formula:

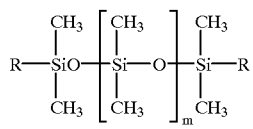

in which m is 100; R is a radical —$(CH_2)_3$—O—$(C_2H_4O)_x$—$(C_3H_6O)_y$—$CH_3$, wherein t ranges from 3 to 100 and u ranges from 1 to 50, the ratio by weight of the number of $C_2H_4O$ structural units to the number of $C_3H_6O$ structural units being approximately 42/58 and the average molecular weight of R ranging from 800 to 1,000.

Exemplary commercially available products which can comprise all or part of the oxyalkylenated silicones substituted at the α- and ω-positions according to the invention, as emulsifiers, are, in particular, those marketed under the trademarks "Abil EM 97" by Goldschmidt or "KF 6009", "X22-4350", "X22-4349" or "KF 6008" by Shin Etsu.

The polyalkylpolyethersiloxane emulsifiers as described above are preferably formulated in a proportion ranging from 0.1% to 30% and more particularly from 0.5% to 10% by weight with respect to the total weight of the emulsion.

To improve the persistence of the coloration on the skin and the fastness towards water of the coloration on the skin, the compositions according to the invention can additionally comprise at least one aqueous dispersion of film-forming polymer particles (latex).

Exemplary such film-forming polymers according to the present invention include synthetic polymers of radical type or of polycondensate type, polymers of natural origin and mixtures thereof.

By the term "radical polymer" is a polymer prepared by polymerization of unsaturated monomers, in particular monomers with ethylenic unsaturation, each monomer being capable of homopolymerizing (unlike polycondensates). The polymers of radical type can be, in particular, vinyl polymers or copolymers, in particular acrylic polymers.

The vinyl polymers can be prepared by the polymerization of ethylenically unsaturated monomers bearing at least one acidic group and/or of the esters of these acidic: monomers and/or of the amides of these acidic monomers.

Exemplary monomers bearing an acidic group are the unsaturated α,ω-ethylenic carboxylic acids, such as acrylic acid, methacrylic acid, crotonic acid, maleic acid or itaconic acid. Preferred are (meth)acrylic acid and crotonic acid and even more preferred is (meth)acrylic acid.

Exemplary esters of acidic monomers include the esters of (meth)acrylic acid (also known as (meth)acrylates,), in particular alkyl (meth)acrylates, especially $C_1$–$C_{20}$ alkyl (meth) acrylates, preferably $C_1$–$C_8$ alkyl (meth)acrylates, aryl (meth)acrylates, in particular $C_6$–$C_{10}$ aryl (meth)acrylates, or hydroxyalkyl (meth)acrylates, in particular $C_2$–$C_6$ hydroxyalkyl (meth)acrylates. Representative of the alkyl (meth)acrylates are methyl methacrylate, ethyl methacrylate, butyl methacrylate, isobutyl methacrylate, 2-ethylhexyl methacrylate and lauryl methacrylate. Representative hydroxyalkyl (meth)acrylates, are hydroxyethyl acrylate, 2-hydroxypropyl acrylate, hydroxyethyl methacrylate and 2-hydroxypropyl methacrylate, and representative aryl (meth)acrylates are benzyl acrylate and phenyl acrylate. The particularly preferred esters of (meth)acrylic acid are the alkyl (meth)acrylates.

According to the present invention, the alkyl group of the esters can be either fluorinated or perfluorinated, namely, a portion or all of the hydrogen atoms of the alkyl group are substituted by fluorine atoms.

And exemplary amides of the acidic monomers are(meth) acrylamides and especially N-alkyl(meth)acrylamides, in particular N-($C_2$–$C_{12}$ alkyl)(meth)acrylamides. Representative N-alkyl(meth)acrylamides include N-ethylacrylamide, N-t-butylacrylamide and N-t-octylacrylamide.

The vinyl polymers can also be prepared via the homopolymerization or copolymerization of monomers selected from among the vinyl esters and styrene monomers. In particular, these monomers can be polymerized with acidic monomers and/or their esters and/or their amides, such as those indicated above. Exemplary vinyl esters include vinyl acetate, vinyl neodecanoate, vinyl pivalate, vinyl benzoate and vinyl t-butylbenzoate. And representative styrene monomers include styrene and α-methylstyrene.

The above list of monomers given is not limiting as any monomer known to this art and falling within the categories of acrylic and vinyl monomers (including monomers modified by a silicone chain) is suitable.

Exemplary acrylic polymers which are useful according to this invention are those marketed under the trademarks Neocryl XK-90®, Neocryl A-1070®, Neocryl BT-62®, Neocryl A-1079® or Neocryl A-523® by Zeneca or Dow Latex 432® by Dow Chemical. Particularly exemplary is the vinyl acetate/vinyl p-(tert-butyl)benzoate/crotonic acid (65/25/10) terpolymer formulated as a 21% by weight aqueous dispersion.

Exemplary polycondensates are the anionic, cationic, nonionic or amphoteric polyurethanes, polyurethane/ acrylics, polyurethane/polyvinyl-pyrrolidones, polyester/ polyurethanes, polyether/polyurethanes, polyureas, polyurea/polyurethanes and mixtures thereof.

The polyurethanes include the aliphatic, cycloaliphatic or aromatic polyureas, polyurea/urethanes or polyurethane copolymers comprising, whether alone or as in admixture:

(a) at least one structural unit of aliphatic and/or cycloaliphatic and/or aromatic polyester origin, and/or, (b) at least one branched or unbranched silicone structural unit, for example polydimethylsiloxane or polymethylphenylsiloxane, and/or (c) at least one structural unit comprising fluorinated moieties.

The polyurethanes according to the invention can also be prepared from branched or unbranched polyesters or from alkyds comprising mobile hydrogens which are modified by reaction with a diisocyanate and a bifunctional organic compound (for example dihydro, diamino or hydroxyamino) additionally comprising either a carboxylic acid or carboxylate group, or a sulfonic acid or sulfonate group, or a neutralizable tertiary amine group or a quaternary ammonium group. Suitable polyurethanes include those marketed under the trademarks Neorez R-981® or Neorez R-974® by the company Zeneca or Sancure 815®, Sancure 875®, Sancure 2060®, Sancure 2255® or Sancure 861® by Sanncor.

Also exemplary of the polycondensates are the polyesters, polyesteramides, fatty-chain polyesters, polyamides and epoxy ester resins.

The polyesters can be prepared in known manner by polycondensation of dicarboxylic acids with polyols, in particular diols. The dicarboxylic acid can be aliphatic, alicyclic or aromatic. Exemplary such acids include oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalene-dicarboxylic acid and 2,6-napthalenedicarboxylic acid.

These dicarboxylic acid monomers can be used either alone or in combination with at least two dicarboxylic acid monomers. Preferred among these monomers are phthalic acid, isophthalic acid and terephthalic acid.

The diol can be selected from among aliphatic, alicyclic or aromatic diols. Preferred diols include ethylene glycol, diethylene glycol, triethylene glycol, 1,3-propanediol, cyclohexanedimethanol and 4-butanediol. And preferred polyols include glycerol, pentaerythritol, sorbitol and trimethylolpropane.

The polyesteramides can be prepared analogously to the polyesters by polycondensation of diacids with diamines or aminoalcohols. Exemplary diamines are ethylenediamine, hexamethylenediamine, meta-phenylenediamine and para-phenylenediamine. A representative aminoalcohol is monoethanolamine.

The polyester can, in addition, comprise at least one monomer bearing at least one $—SO_3M$ group, with M representing a hydrogen atom, an ammonium ion $NH_4^+$ or a metal ion, such as, for example, an $Na^+$, $Li^+$, $K+$, $Mg^{2+}$, $Ca^{2+}$, $Cu^{2+}$, $Fe^{2+}$ or $Fe^{3+}$ ion. Preferred are bifunctional aromatic monomers comprising such an $—SO_3M$ group.

The aromatic nucleus of the bifunctional aromatic monomer additionally bearing an $—SO_3M$ group as described above is advantageously selected, for example, from among benzene, naphthalene, anthracene, diphenyl, oxydiphenyl, sulfonyldiphenyl and methylenediphenyl nuclei. Also exemplary bifunctional aromatic monomers additionally bearing an $—SO_3M$ group are sulfoisophthalic acid, sulfoterephthalic acid, sulfophthalic acid and 4-sulfonaphthalene-2,7-dicarboxylic acid.

Copolymers based on isophthalate/sulfoisophthalate and more particularly copolymers prepared by condensation of diethylene glycol, cyclohexanedimethanol, isophthalic acid and sulfoisophthalic acid are particularly representative. Such polymers Eire marketed, for example, under the trademark Eastman AQ by Eastman Chemical.

The optionally modified polymers of natural origin are advantageously selected from among shellac resin, sandarac gum, dammars, elemis, copals, water-insoluble cellulose polymers and mixtures thereof.

And exemplary polymers prepared via radical polymerization of one or more radical monomers inside and/or partially at the surface of pre-existing particles of at least one polymer are selected from among the polyurethanes, polyureas, polyesters, polyesteramides and/or alkyds. These polymers are generally known as hybrid polymers.

The dispersion comprising one or more film-forming polymers can be formulated by one skilled in this art on the basis of his overall knowledge. The size of the polymer particles in aqueous dispersion advantageously ranges from 10 to 500 nm and preferably from 20 to 150 nm.

The film-forming polymer in aqueous dispersion is advantageously present in the compositions according to the invention in a content ranging from 1% to 60% by weight, preferably from 5% to 40% by weight, on a dry basis of film-forming polymers with respect to the total weight of the composition.

The cosmetic and/or dermatological compositions of the present invention can comprise one or more organic solvents, such as, for example, a lower $C_2$–$C_6$ monoalcohol, such as ethanol or isopropanol; or a polyol, such as glycerol, butylene glycol, isoprene glycol or propylene glycol.

Too, the cosmetic and/or dermatological compositions of the present invention can additionally comprise one or more hydrophilic or lipophilic sunscreening agents active in the UVA and/or UVB (absorbers)ranges. These screening agents include, in particular, cinnamic derivatives, salicylic derivatives, dibenzoylmethane derivatives, benzylidenecamphor derivatives, benzimidazole derivatives, triazine derivatives, beznzophenone derivatives, $\beta,\beta'$-diphenylacrylate derivatives, p-aminobenzoic acid derivatives or the polymer screening agents and silicone screening agents described in WO-93/04665. Other examples of organic screening agents are described in EP-A-0,487,404.

The cosmetic and/or dermatological compositions according to the invention can also comprise pigments or alternatively nanopigments of metal oxides, which may or may not be coated, other than those of the invention, such as, for example, titanium dioxide (amorphous or crystallized in the rutile and/or anatase form), zinc oxide, zirconium oxide or cerium oxide nanopigments. Conventional coating agents include, furthermore, alumina and/or aluminum stearate, or silicones. Such metal oxide nanopigments, which may or may not be coated, are particularly described in EP-A-0, 518,772 and EP-A-0,518,773.

The compositions of this invention can also comprise thickeners, which can be selected, in particular, from among the crosslinked polyacrylic acids; fatty-chain polyacrylic acids; guar and cellulose gums, which may or may not be modified, such as hydroxypropylated guar gum, methylhydroxyethylcellulose and hydroxypropylmethyl cellulose; or modified clays, such as modified magnesium silicate (bentone gel VS38 marketed by Rheox) or hectorite modified with distearyldimethyl-ammonium chloride (bentone 38 CE marketed by Rheox).

The compositions of the present invention can also comprise fillers commonly used in cosmetic compositions. The preferred fillers can be inorganic or synthetic, lamellar or non-lamellar. Exemplary are talc, mica, silica, kaolin, teflon, starch, natural mother-of-pearl, boron nitride, microspheres, such as Expancel (NobeL Industrie), or microsponges, such as polytrap (Dow Corning). Preferred are spherical fillers having a size of less than 25 μm, such as polyethylene powders, nylon powders, silicone resin microbeads (Tospearls marketed by Toshiba) or silica microspheres.

The compositions of this invention can additionally comprise conventional cosmetic and/or dermatological adjuvants and additives selected in particular from among softeners, antioxidants, agents for combating free radicals, opacifiers, stabilizers, emollients, hycdroxy acids, antifoaming agents, moisturizing agents, vitamins, ceramides, fragrances, preservatives, surfactants, sequestering agents, polymers, propellants, basifying or acidifying agents, colorants or any other ingredient commonly formulated into water-in-oil emulsions for the artificial coloration or tanning of the skin.

It will off course be appreciated that one skilled in this art will take care to select the optional additional compound or compounds indicated above and/or the amounts thereof such that the advantageous properties intrinsically associated with the water-in-oil emulsions based on iron oxide nanopigments in accordance with the invention are not, or not substantially, detrimentally affected by the envisaged addition or additions.

The compositions of the present invention can be provided in the form of creams, milks, gels, cream gels, ointments, fluid lotions, vaporizable fluid lotions or any other form generally used in cosmetics, in particular that typically suitable for cosmetic compositions for the artificial coloration of the skin.

The compositions according to the invention can be formulated via techniques well known to this art, in particular those intended for the preparation of emulsions of water-in-oil type.

The present invention thus features water-in-oil emulsions as described above comprising at least one iron oxide nanopigment, providing cosmetic and/or dermatological compositions suited for imparting to the skin an artificial coloration similar to natural tanning.

Too, the present invention features a regime/regimen for the artificial coloration of human skin similar to natural tanning, comprising topically applying thereto an effective artificial tanning amount of a cosmetic composition as described above.

In order to further illustrate the present invention and the advantages thereof, the following specific examples are given, it being understood that same are intended only as illustrative and in nowise limitative.

EXAMPLES

This example relates to demonstrating, by an in vivo evaluation method, the intensity, the persistence and the fastness towards water of the coloration provided by a composition A in the form of a water-in-oil emulsion comprising iron oxide nanopigments, as well as the speed with which such coloration develops.

Second, the improvement, in terms of transparency and of coloration power, contributed by the composition A with respect to a conventional composition B of the prior art in the form of a water-in-oil emulsion comprising iron oxide pigments has been demonstrated by an in vitro evaluation method.

The following composition A was prepared:

| Composition A: | |
|---|---|
| (i) Oxyalkylenated silicone substituted at the α and ω positions, marketed under the trademark "Abil EM 97" by Goldschmidt | 6.0 g |
| (ii) Isostearyl diglyceryl succinate, marketed under the trademark "Imwitor 780 K" by Hüls | 2.0 g |
| (iii) Butyl p-hydroxybenzoate | 0.015 g |
| (iv) Polydiphenyldimethylsiloxane/cyclopentadimethylsiloxane mixture, marketed under the trademark Mirasil C-DPDM by Rhodia Chimie | 8.0 g |
| (v) Cyclomethicone, marketed under the trademark DC245 Fluid by Dow Corning | 14.0 g |
| (vi) Modified hectorite | 4.0 g |
| (vii) Isododecane | 5.0 g |
| (viii) Nylon powder | 8.0 g |
| (ix) Coated red iron nanooxide (31 nm) as a 40% dispersion in DC345, marketed under the trademark "Nanoguard WCD 2015" by Nanophase Technologies | 3.0 g |
| (x) Black iron nanooxide (23 nm), marketed under the trademark "Nanoguard FE45BL" by Nanophase Technologies | 0.3 g |
| (xi) Ethyl alcohol | 5.0 g |
| (xii) Magnesium sulfate | 0.7 g |
| (xiii) Diisopropyl adipate | 1.0 g |
| (xiv) Vinyl acetate/vinyl | 20.0 g |

-continued

| Composition A: | |
|---|---|
| p-(tert-butyl)-benzoate/crotonic acid (65/25/10) copolymer as a 21% aqueous dispersion, which copolymer was partially neutralized and stabilized | |
| (xv) Preservative | 0.25 g |
| (xvi) Demineralized water | 22.73 g |

(I) In Vivo Evaluation Method:

The composition A was applied at the rate of 2 mg/cm$^2$ to an area of 2.5×2.5 cm$^2$ defined on the backs of the forearms of 4 volunteers.

The six series of calorimetric measurements which follow were carried out using a Minolta CM-1000 calorimeter:
(1) before application of the composition ($T_0$),
(2) 15 minutes after application ($T_{15\ min}$);
(3) 1 hours after application ($T_1h$);
(3) 3 hours after application ($T_3h$);
(3) 5 hours after application ($T_5h$);
(3) 24 hours after application ($T_{24}h$);
(3) 24 hours after application and after washing ($T_{24\ H\ washing}$).

The results, as mean values, are expressed in the (L*, a*, b*) system, in which L* represents the brightness, a* represents the red-green axis (−a*=green, +a*=red) and b* represents the yellow-blue axis (−b*=blue, +b*=yellow). Thus, a* and b* express the hue of the skin.

The matters of interest in evaluating the intensity of the coloration were:
(a) the ΔL*=L* (T)−L*($T_0$), which reflects the darkening in the coloration; the more negative the ΔL*, the more the color has darkened,
(b) the corresponding Δa* and Δb*;
(c) the corresponding Δa*/Δb* ratios, which reflect the red-yellow balance and therefore the hue: the closer the Δa*/Δb* to 1, the more natural the hue.

The results obtained are reported in the following Table (I):

TABLE (I)

| Time elapsed after application of the composition A | ΔL* = L* (T) − L* ($T_0$) | Δa*/Δb* |
|---|---|---|
| 15 min | −10.43 | 0.82 |
| 1 h | −9.12 | 0.79 |
| 3 h | −8.87 | 0.82 |
| 5 h | −8.68 | 0.9 |
| 24 h | −3.94 | 0.79 |
| 24 h with washing | −1.52 | 0.88 |

The value of ΔL* obtained 15 minutes after application of the composition A according to the invention was already −10.43; this demonstrates a rapid and satisfactorily intense darkening of the skin.

The values of ΔL* obtained 24 hours after application of the composition A according to the invention were −3.94 (without washing) and −1.52 (with washing); this reflects a coloration on the skin which is persistent over time and resistant to water.

The Δa*/Δb* ratios, measured after 15 min, 1 h, 3 h, 5 h, 24 h and 24 h after washing, vary from 0.82 to 0.9; these results evidenced that the coloration obtained exhibits a very stable hue, similar to the natural coloration of the skin, which is constant over time and resistant to water.

(II) In Vitro Evaluation Method:

A composition B was also formulated (not according to the invention) which was identical to the composition A, but which contained, instead of the iron oxide nanopigments:
  (i) 3 g of pigmentary black iron oxide (2.7 μm), marketed under the trademark "Cosmetic Black C33-5198 (Sun)" by Sun; and
  (ii) 0.3 g of pigmentary brown iron oxide (1.9 μm), marketed under the trademark "Sicomet brun ZP3569" [Sicomet brown ZP3569] by BASF.

In order to evaluate the transparency and coloring power contributed by each of the formulations A and B, the characterization method employed in the paint industry was employed, described in the text "Industrial Color Testing" by Hans G. Volz, pages 101–111, published by VCH.

Films having different thickness formed from each tested composition A and B: 12, 30 and 60 μm, were spread over a standardized contrast plate having a chronometrically calibrated black area and a colorimetrically calibrated white area.

The following calorimetric measurements were carried out using a Minolta CM-1000 calorimeter:
(1) before application of the composition ($T_0$),
(2) after the application, after 15 min ($T_{15\ min}$).

The results are expressed in the (L*, a*, b*) system, in which L* represents the brightness, a* represents the red-green axis (−a=green, +a=red) and b* represents the yellow-blue axis (−b*=blue, +b*=yellow). Thus, a* and b* express the hue of the film on the plate.

The matters of interest in evaluating the transparency or the coloring power of the film applied were:

(a) $\Delta L^* = L(T_{15\ min}) - L(T_0)$ (b) the corresponding $\Delta a^*$ and $\Delta b^*$, (c) the $\Delta E_{ab}^* = \sqrt{\Delta a^{*2} + \Delta b^{*2} + \Delta L^{*2}}$ (1) Transparency:

The transparency is characterized by the variation in $\Delta E_{ab}^*$ as a function of the thickness of the film, when the $\Delta E_{ab}^*$ is measured on a black background. The higher the value of the $\Delta E_{ab}^*$, the more the applied product is opacifying.

The results obtained are reported in the following Table (II):

TABLE (II)

| Thickness | ΔL* | Δa* | Δb* | $\Delta E_{ab}^*$ |
|---|---|---|---|---|
| COMPOSITION A (invention) | | | | |
| 12 μm | 14.393 | 1.757 | 6.453 | 15.871 |
| 30 μm | 16.723 | 3.657 | 8.793 | 19.245 |
| 60 μm | 19.083 | 7.027 | 12.573 | 23.909 |
| COMPOSITION B (not according to the invention) | | | | |
| Thickness | ΔL | Δa* | Δb* | $\Delta E_{ab}^*$ |
| 12 μm | 22.363 | 13.647 | 11.223 | 28.501 |
| 30 μm | 25.443 | 18.197 | 15.203 | 34.780 |
| 60 μm | 25.823 | 19.617 | 16.263 | 36.279 |

It was determined:
  (a) that the composition B applied to the black substrate in the proportion of a 12 μm layer was already, at this amount, twice as opacifying as the composition A of the invention applied under the same conditions;
  (b) that the variation $\Delta E_{ab}^*$ as function of the thickness of the film was much greater with the composition B (iron oxide of micrometric size) and that the latter proved to be more covering, more capable of opacifying the substrate on which it was deposited, than the composition A according to the invention comprising the iron oxides of nanometric size.

(2) Coloring Power:

The coloring power was characterized by the variation in the $\Delta E_{ab}^*$ as a function of the thickness of the film, when $\Delta E_{ab}^*$ was measured on a white background. The higher the value of the $\Delta E_{ab}^*$, the greater the tendency of the film to color the plate.

The results obtained are reported in the following Table (III):

TABLE (III)

| Thickness | ΔL | Δa | Δb | $\Delta E_{ab}^*$ |
|---|---|---|---|---|
| COMPOSITION A (invention) | | | | |
| 12 μm | −22.56 | 22.793 | 40.753 | 51.86 |
| 30 μm | −32.69 | 30.193 | 44.043 | 62.61 |
| 60 μm | −40.84 | 34.233 | 40.453 | 66.9 |
| COMPOSITION B (not according to the invention) | | | | |
| 12 μm | −14.56 | 14.283 | 12.103 | 23.717 |
| 30 μm | −42.27 | 25.293 | 18.313 | 52.554 |
| 60 μm | −47.60 | 25.353 | 17.593 | 56.728 |

It was determined:
  (a) that the composition A of the invention applied to the white substrate in the proportion of a 12 μm layer was already, at this amount, approximately twice as coloring as the composition B applied under the same conditions;
  (b) that the variation in $\Delta E_{ab}^*$ as function of the thickness was much faster and greater with the composition A (iron oxide of nanometric size), and therefore exhibited a greater dyeing power, than the composition B comprising iron oxides of micrometric size.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for the artificial tanning and/or darkening of human skin, comprising an effective artificial tanning/darkening amount of particulates of at least one iron oxide nanopigment, the mean size of the primary particles of which nanopigment particulates being less than 100 nm, the particulates of said at least one iron oxide nanopigment being formulated into a vehicle, diluent or carrier therefor which comprises a water-in-oil emulsion, and said particulates comprising greater than 2% by weight of the total weight of such cosmetic/dermatological composition.

2. The cosmetic/dermatological composition as defined by claim 1, the mean size of the primary particles of which iron oxide nanopigment particulates ranging from 5 nm to 50 nm.

3. The cosmetic/dermatological composition as defined by claim 1, the mean size of the primary particles of which iron oxide nanopigment particulates ranging from 10 nm to 30 nm.

4. The cosmetic/dermatological composition as defined by claim 1, said iron oxide nanopigment particulates comprising up to 10% by weight of the total weight thereof.

5. The cosmetic/dermatological composition as defined by claim 1, said iron oxide nanopigment particulates comprising from 3% to 6% by weight of the total weight thereof.

6. The cosmetic/dermatological composition as defined by claim 1, said water-in-oil emulsion comprising a water-in-silicone oil emulsion.

7. The cosmetic/dermatological composition as defined by claim 6, said water-in-oil emulsion comprising a water-in-volatile silicone oil emulsion.

8. The cosmetic/dermatological composition as defined by claim 6, said water-in-silicone oil emulsion comprising at least one silicone oil selected from among at least one optionally functionalized linear polydiorganosiloxane, at least one cyclic polydiorganosiloxane, at least one optionally crosslinked organopolysiloxane, or mixture thereof.

9. The cosmetic/dermatological composition as defined by claim 6, said water-in-silicone oil emulsion comprising at least one linear polydiorganosiloxane having the structural formula:

$$X-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-X$$

in which X is a radical —$CH_3$ or OH, and n is an integer ranging from 0 to 2,000.

10. The cosmetic/dermatological composition as defined by claim 6, said water-in-silicone oil emulsion comprising at least one cyclic polydiorganosiloxane having the structural formula:

$$\left[\underset{\underset{CH_3}{|}}{\overset{\overset{CH_3}{|}}{Si}}-O\right]_n$$

in which n is an integer ranging from 3 to 8.

11. The cosmetic/dermatological composition as defined by claim 1, comprising at least one silicone emulsifying agent.

12. The cosmetic/dermatological composition as defined by claim 11, said at least one silicone emulsifying agent comprising a polyalkylpolyethersiloxane having polyoxyethylene and polyoxypropylene chains grafted onto the backbone or endgroups thereof.

13. The cosmetic/dermatological composition as defined by claim 11, said at least one silicone emulsifying agent having the structural formula (I):

$$R_1-\underset{\underset{R_1}{|}}{\overset{\overset{R_1}{|}}{Si}}-O-\left[\underset{\underset{R_2}{|}}{\overset{\overset{R_1}{|}}{Si}}-O\right]_p-\left[\underset{\underset{R_4}{|}}{\overset{\overset{R_1}{|}}{Si}}-O\right]_n-\underset{\underset{R_1}{|}}{\overset{\overset{R_1}{|}}{Si}}-R_1 \quad (I)$$

in which $R_1$ and $R_4$, which may be identical or different, are each a hydrogen atom, a linear or branched $C_1$–$C_{30}$ alkyl radical or a phenyl radical; the radicals $R_2$, which may be identical or different, are each a radical —$(C_xH_{2x})$—$(OC_2H_4)_a$—$(OC_3H_6)_b$—$OR_3$, wherein the radicals $R_3$, which may be identical or different, are each a hydrogen atom, a linear or branched alkyl radical having from 1 to 12 carbon atoms, or a linear or branched acyl radical, having from 2 to 12 carbon atoms; n ranges from 1 to 1,000; p ranges from 1 to 30; a ranges from 1 to 50; b ranges from 1 to 50; and x ranges from 1 to 5.

14. The cosmetic/dermatological composition as defined by claim 13, wherein formula (I), the radicals $R_1$ and $R_4$ are each methyl radicals and $R_3$ is a hydrogen atom.

15. The cosmetic/dermatological composition as defined by claim 13, said polyalkylpolyethersiloxane having a number-average molecular weight greater than 30,000 and wherein n is about 396, p is about 4, a is about 18 and b is about 18.

16. The cosmetic/dermatological composition as defined by claim 13, wherein formula (I), the radicals $R_1$ are each methyl radicals and the radicals $R_4$ are lauryl radicals.

17. The cosmetic/dermatological composition as defined by claim 11, said at least one silicone emulsifying agent having the structural formula (II):

$$R-\underset{\underset{R^2}{|}}{\overset{\overset{R^2}{|}}{Si}}-O-\left[\underset{\underset{R^2}{|}}{\overset{\overset{R^2}{|}}{Si}}-O\right]_m-\underset{\underset{R^2}{|}}{\overset{\overset{R^2}{|}}{Si}}-R \quad (II)$$

in which R is a radical —$(CH_2)_sO$—$(C_2H_4O)_t(C_3H_6O)_uR^1$ wherein $R^1$ is H, $CH_3$ or $CH_2CH_3$, s is an integer ranging from 1 to 5, t ranges from 1 to 100 and u ranges from 0 to 50, with the proviso that the $(C_2H_4O)$ and $(C_3H_6O)$ structural units may be distributed randomly or in blocks; the $R^2$ radicals are each a $C_1$–$C_3$ alkyl radical or a phenyl radical, and $5 \geq m \geq 300$.

18. The cosmetic/dermatological composition as defined by claim 12, said polyalkylpolyethersiloxane comprising from 0.5% to 10% by weight thereof.

19. The cosmetic/dermatological composition as defined by claim 1, further comprising at least one latex of film-forming polymer particles.

20. A regime/regimen for artificially tanning and/or darkening human skin, comprising topically applying thereto, for such period of time as required to elicit the desired effect, the cosmetic/dermatological composition as defined by claim 1.

21. The cosmetic/dermatological composition as defined by claim 1, comprising a cream, gel, ointment, lotion, milk or cream gel.

22. The cosmetic/dermatological composition as defined by claim 1, further comprising a UV-A and/or UV-B sunscreen.

23. The cosmetic/dermatological composition as defined by claim 1, further comprising at least one cosmetically/dermatologically acceptable adjuvant or additive.

* * * * *